United States Patent [19]
Hamburger et al.

[11] Patent Number: 5,986,555
[45] Date of Patent: Nov. 16, 1999

[54] ALLERGEN DETECTOR SYSTEM AND METHOD

[75] Inventors: Robert N. Hamburger, 9485 La Jolla Shores Dr., La Jolla, Calif. 92037; Jien-Ping Jiang, Tuscon, Ariz.; Ruibo Wang, Goleta, Calif.; Donald F. Kaminski, deceased, late of Hattiesburg, Mich., by Alice Mae Smith Kaminski, administratrix

[73] Assignee: Robert N. Hamburger, La Jolla, Calif.

[21] Appl. No.: 08/946,288

[22] Filed: Oct. 7, 1997

[51] Int. Cl.$^6$ ..................................................... G08B 21/00

[52] U.S. Cl. .......................... 340/627; 340/630; 116/214; 250/564; 250/574; 356/438

[58] Field of Search ..................................... 340/627, 630; 250/564, 565, 574; 356/337, 339, 439, 438; 116/214; 73/28.01, 28.04, 863.21–863.24

[56] References Cited

U.S. PATENT DOCUMENTS

| | | | |
|---|---|---|---|
| 4,245,910 | 1/1981 | Kallander | 340/627 |
| 5,001,463 | 3/1991 | Hamburger | 340/627 |
| 5,646,597 | 7/1997 | Hamburger et al. | 340/627 |

*Primary Examiner*—Daniel J. Wu
*Attorney, Agent, or Firm*—Brown, Martin, Haller & McClain, LLP

[57] ABSTRACT

An allergen particle detecting apparatus has a sample area through which environmental air is directed. A light beam is directed through the air sample so that portions of the beam will be scattered if any particles are present in the path of the beam. A beam blocking device on the opposite side of the air sample is arranged to block all light except light scattered in a predetermined angular range corresponding to a predetermined allergen particle size range. Light transmitted through the blocking device is detected by a light detector and an alarm output signal is produced if the detected amount of light is above a predetermined level.

23 Claims, 1 Drawing Sheet

AIR FLOW

ALLERGEN DETECTOR SYSTEM AND METHOD

RELATED APPLICATIONS

This application includes subject matter that may be related to co-pending and commonly assigned application Ser. No. 08/771,641, filed Dec. 20, 1997, the disclosure of which is incorporated herein.

BACKGROUND OF THE INVENTION

The present invention is directed to a system and method for detecting airborne allergen particles and for providing an alarm or operating a filtering system if the detected amount of allergen particles is above a predetermined level.

Many individuals suffer from allergies to airborne particles such as dust, pollen and the like which are often present in the environmental air breathed by the individual. The majority of particulates to which many individuals are sensitive are typically in the 5 to 50 micron range. The presence of such particles in air breathed by sensitive or allergic individuals may give rise to a plethora off symptoms such as asthma, coughing, sneezing, as well as skin rashes and anaphylaxis. Knowledge or warning of the presence of high levels of allergenic particles in the environmental air is helpful to such individuals, potentially enabling them to take medication, leave the area, or activate allergen removing filters before the onset of serious symptoms.

In U.S. Pat. No. 5,001,463 (Hamburger) an allergen particulate detecting apparatus is described wherein air is blown through a passageway in which an allergen particle sensor is mounted for sensing allergen-sized particles. The output signal of the sensor is dependent on the amount of sensed particles, and an alarm is activated if the signal is above a predetermined level.

U.S. Pat. No. 5,646,597 (Hamburger, et al.) describes a system and method for detecting concentrations of particles in a given range of sizes by directing a light beam through a sample of environmental air and measuring the amount of light which is scattered by particles within the sample. A beam blocking device is provided which blocks the focused, unscattered portion of the light beam. A discriminator is also provided which allows the device to detect only those particles which are within the size range of approximately 5 to 50 microns. Pending application Ser. No. 08/771,641 providing an improvement in the discriminating apparatus of the '597 patent.

One problem with the devices described in the prior art which utilizes lasers arises when an inexpensive laser is used as the light source. In addition to the light that is focused on the beam blocking device, a certain amount of light "noise" is also produced. This noise can cause false readings if mistaken by the detector for light scattered by particles in the air sample. The present invention describes an optical configuration wherein the light noise produced by the laser is also blocked, thus preventing the device from detecting the noise as light scattered by particles in the air sample.

SUMMARY OF THE INVENTION

In the present invention, an allergen particle detection system is provided which comprises a light source for directing a light beam through a sample of environmental air, and a beam blocking and focusing assembly positioned in the light path on the opposite side of the air sample which blocks the transmission of all light, including noise generated by the light source, except the portion of light scattered in a predetermined angular range. The scattered light is focused on a detector positioned to receive light transmitted through the beam blocking assembly, and a control circuit is connected to the detector for generating an alarm output signal if the detector output is above a predetermined level.

The alarm output signal may be used to activate an audible or visual alarm device, or to turn on a filtration and ventilation system including HEPA or allergen particle filters. The filtration system may be turned off as soon as the detected allergen particles have returned to a safe level. The apparatus may be relatively small, and may be conveniently designed for wall mounting.

In the preferred embodiment, the allergen detection device is contained in a darkened tube-like housing. The laser light source is disposed at one end of the housing and transmits a light beam through a sample of environmental air which has been refreshed by a fan mounted in the side of the housing. The beam blocking and focusing assembly is disposed opposite the air sample from the laser and comprises two lenses mounted on the optical axis of the device such that the scattered light is transmitted through both lenses and focused on an optical detector. The first lens has a circle of light blocking material centered on the optical axis of the device. The light blocking material is of a predetermined diameter sized to block all unscattered light from the laser, and light scattered at angles below a predetermined minimum angle, which is scattered by particles larger than the largest allergen particle size. Scattered light which exceeds the maximum scattering angle is absorbed by the darkened walls of the detector housing and are thereby also effectively blocked. The first lens transmits scattered light that falls within the predetermined angular range through to the second lens, which focuses it on an optical detector mounted at the end of the housing opposite the laser light source. Noise which is emitted by the laser is focused by the first lens onto a circle of light blocking material which is mounted on the second lens on the optical axis of the device. The noise is thereby prevented from being focused on the optical detector by the second lens and is effectively blocked.

In the preferred embodiment, the dimensions of the blocking and focusing assembly were arranged to block all light except that scattered by particles in the size range of 5 to 50 microns.

According to another aspect of the present invention, a method of detecting the presence and concentration of allergen particles in the air is provided which comprises the steps of directing a light beam through a sample of environmental air such that light will be scattered by any particles in the air, blocking unscattered light, light scattered outside a predetermined angle range and noise produced by the light source, transmitting only light within the predetermined range of scattering angle, focusing the transmitted light, detecting the focused, transmitted light and producing an output signal at a level proportional to the amount of light transmitted, and generating an alarm signal if the output signal is above a predetermined level.

This system and method readily discriminates between allergen size particles in the 5 to 50 micron range and larger, non-allergenic particles so as to produce an accurate indication of the allergen particle levels in a room or enclosed area. Preferably, the level at which the alarm signal is produced is adjustable. The apparatus can be readily connected to turn on auxiliary air cleaning appliances or filters such as HEPA filters.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENTS

Figure 1:
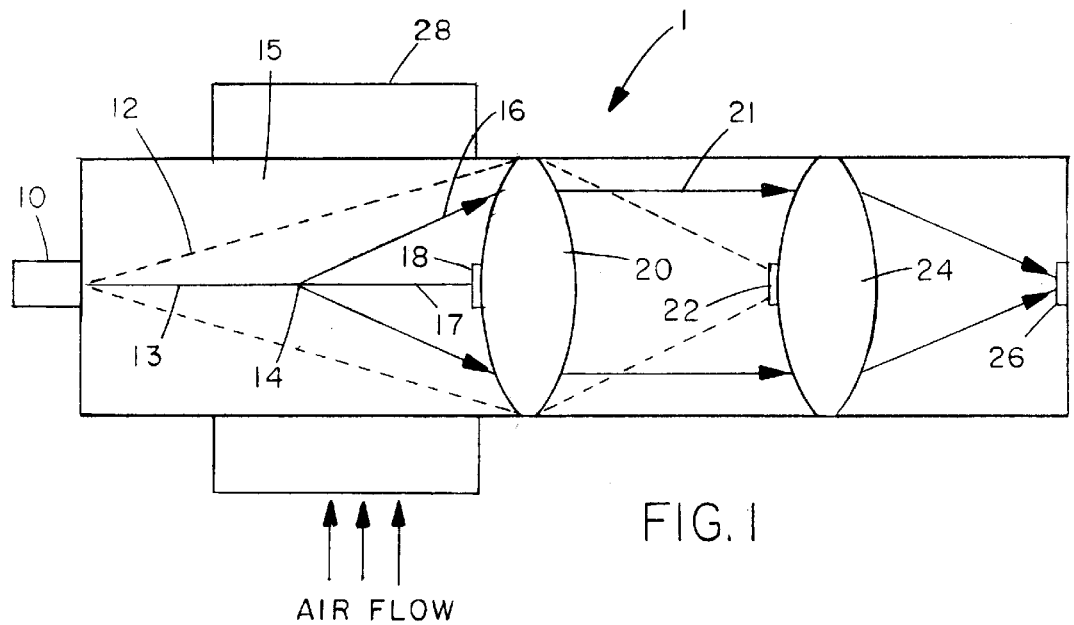
FIG. 1 is a schematic block diagram of the optical system.

FIGS. 1 and 2 of the drawings illustrate an allergen particle detector apparatus 1 according to the preferred embodiment of the present invention. Referring to FIG. 1, the apparatus comprises light source 10, which is preferably a laser. Light source 10, in the preferred embodiment is a 660 nanometer wavelength laser diode, but, as recognized by one skilled in the art, an inexpensive laser diode of any wavelength could be used with equal success. Although a laser diode in the infrared or visible light range is used as the light source in the preferred embodiment of the invention, other light sources may be used such as other types of laser emitters, for example a He—Ne laser with a wavelength of 0.6328 micron, or other light sources with collimators for producing a coherent light beam, such as light emitting diodes in the visible or infrared light range. The light is preferably infrared, but may alternatively be visible light.

Light source 10 shines focused light beam 13 through air sample 15 within detector 1. When focused light beam 13 strikes particle 14 within air sample 15, a portion of focused light beam 13 is deflected or scattered. The scattered portion 16 of focused light beam 13 thus represents the presence of a particle within air sample 15. The unscattered portion 17 of focused light beam 13 is blocked from reaching detector 26 by circular member 18, which, in the preferred embodiment is a black piece of vinyl adhered to lens 20. Circular member 18 must have a diameter which is greater than or equal to the diameter of focused light beam 13. In the preferred embodiment, the diameter of circular member 18 is approximately 15 mm, or about 2 mm greater than the diameter of focused light beam 13. It is desirable to make the diameter of circular member 18 larger than the diameter of focused light beam 13 to allow for variations in the diameter of focused light beam 13 due to deviations from the manufacturing specifications of light source 10 from unit to unit.

Light source 10, in addition to focused light beam 13, also generates a certain amount of noise 12 from the surface thereof. Noise 12 is focused by lens 20 onto circular member 22, where it is blocked from reaching detector 26. In the preferred embodiment, lens 20 is approximately 40 mm in diameter, has a focal length of 40 mm and is located approximately 80 mm from the surface of light source 10. Circular member 22 is identical to circular member 18, except that it is adhered to lens 24 instead of lens 20.

Scattered portion 16 of focused light beam 13 is transmitted through lens 20, shown in FIG. 1 as 21. Lens 24 focuses transmitted scattered light 21 onto detector 26. In the preferred embodiment, lens 24 is identical to lens 20 and is located approximately 137 mm from light source 10. Detector 26, in the preferred embodiment, is located approximately 173 mm from light source 10.

Detector 26 is a standard, commercially available photodetector which produces a voltage that is a function of the quantity of light which falls upon it. Light source 10, circular member 18, lens 20 circular member 22, lens 24 and detector 26 are aligned with each other along a common axis, and can be mounted in housing 30 such as is shown in FIG. 2.

Figure 2A:
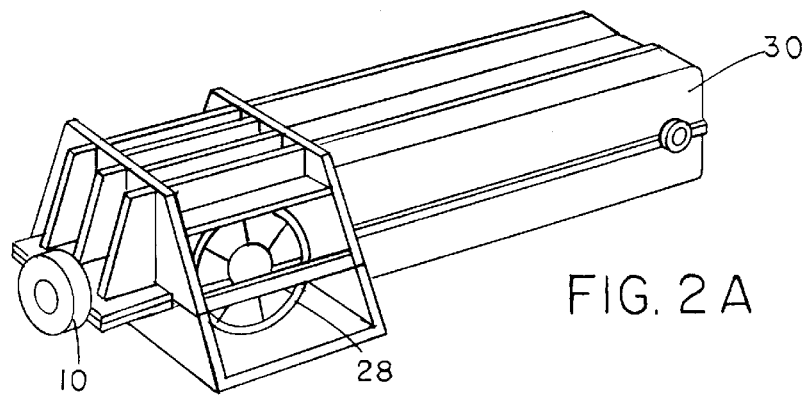
FIG. 2a is a perspective view of the exterior of the allergen detector housing.
Figure 2B:
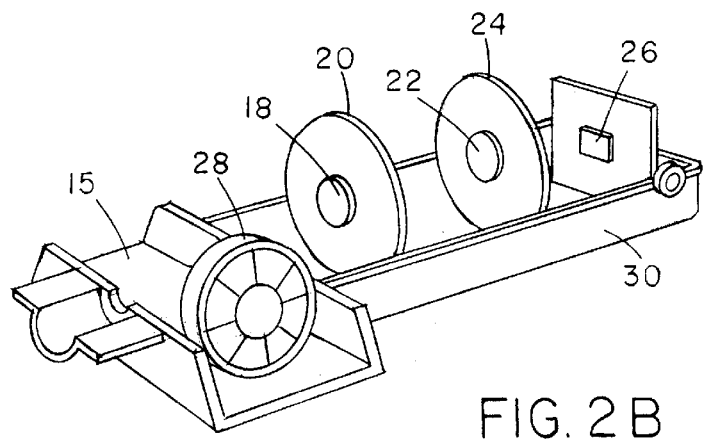
FIG. 2b is a view of the allergen detector with the top portion of the housing removed, revealing the internal elements thereof.

As shown in FIGS. 2a and 2b, fan 28 is used to periodically refresh air sample 15 within housing 30. In the preferred embodiment, air sample 15 is refreshed approximately every 30 seconds.

The output voltage of detector 26, in the preferred embodiment, is converted into a series of pulses over time, which are in turn counted by a logic circuit. An alarm is generated when a certain number of pulses are counted within a certain period of time. This alarm can be used, as in one embodiment of this invention, to provide an indication of poor air quality to a user of the device. In the preferred embodiment of this invention, the alarm is used to turn on an air filter having a blower and a HEPA filtration element. The unit is provided with a sensitivity level setting which can be used to vary the particle concentration within air sample 15 which must be detected before the alarm is generated and the unit turned on. In addition, an ionizer may be provided to negatively charge any particles which may not have been filtered by the filter element, and a manual override to allow the operation of the air filter independently of the allergen detection apparatus.

Housing 30, as shown in FIGS. 2a and 2b, consists of a generally tube-shaped casing in which the elements are mounted. An area is provided wherein an air sample 15 is drawn by fan 28. Preferably, the interior surface of housing 30 is finished to minimize the amount of light reflected therefrom, for, example, as a black matte finish, such that light scattered at or above the maximum scattering angle is absorbed by the walls of housing 30 and not reflected back into lens 20.

The majority of allergen particles to which individuals may be sensitive are in the size range of 5 to 50 microns, although a small quantity of allergen particles may be found at sized from 0.5 to 5 microns and from 50 to 500 microns. Thus, substantially all allergen particles will be found in the size range of 0.5 to 500 microns, with the maximum number being in the range of 5 to 50 microns. Therefore, the apparatus is preferably designed to detect particles in the size range of 0.5 to 500 microns.

The angle at which light is scattered by a particle 14 will be dependent on the wavelength of the light and the size of the particle. Airborne particles of different sizes have quite different light scattering properties. Larger particles will scatter light at smaller angles. For a red to infrared light source in the wavelength range of 0.6 micron to 1.0 micron, the smallest scattering angle for a particle size range of 0.5 to 50 microns is about 4° to 5° (see *Electromagnetc Scattering*, R. L. Rowell and R. S. Stein, ed., p. 140, Gordon and Breach 1965). If circular member 18 is at a distance of L from the air sample, the radius of the central blocking portion should be L * tan (5°), in order to block light scattered at angles less than 5°, i.e. light scattered by particles larger than 50 microns. The blocking device can therefore be arranged to block all light scattered by particles of size greater than 50 microns.

Airborne particles are typically present in the air in a large range of sizes. As noted above, allergen particles such as pollen, dust, mold spores and the like are predominantly in the size range from 5 to 50 microns. Larger particles typically cannot pass through the nose and do not normally cause any problem. The system as illustrated in FIG. 1 is designed to discriminate between light scattered by particles in the allergen size range and light scattered by larger particles outside that range. Only particles with sizes comparable to the wavelength of the incident light will have well pronounced scattering maxima in the forward direction of light propagation.

This apparatus enables up to 99% of airborne allergen particles to be detected, while larger, non-allergenic particles are not detected due to the design of the optical system for eliminating light scattered by particles of sizes outside the allergen size range of 0.5 to 50 microns. The user may readily adjust the allergen detection level. The apparatus is easy and inexpensive to manufacture, and simple to operate. It provides real time, accurate detection of excessive levels of allergen particles in the air, providing a warning to sensitive individuals who may need medication and also allowing allergen filtering equipment to be activated under such conditions to clean the air.

Although preferred embodiments of the present invention have been described above by way of example only, it will be understood by those skilled in the field that modifications may be made to the disclosed embodiments without departing from the scope of the invention, which is defined by the appended claims.

We claim:

1. A device for detecting allergen particles in environmental air comprising:
   a light source for directing a focused beam of light through a sample of said environmental air, whereby portions of said beam of light are scattered at various angles by particles of various sizes present in said sample of environmental air and whereby a portion of said beam of light remains unscattered;
   a beam blocking device for blocking said unscattered portion of said beam of light;
   means for filtering noise generated by said light source;
   a detector for measuring the quantity of light scattered by said particles in said sample of environmental air; and
   means for directing said scattered light to said detector.

2. The device of claim 1 wherein said light source has an optical axis and wherein said beam blocking device comprises a first circular member centered on said optical axis, said first circular member being of a diameter greater than or equal to the diameter of said focused beam of light, said first circular member being opaque to light of the wavelength emitted by said light source.

3. The device of claim 1 wherein said means for filtering comprises a first lens which focuses said noise onto a second circular member centered on said optical axis, said second circular member being opaque to light of the wavelength emitted by said light source and wherein said first lens transmits said scattered light such that said scattered light is not blocked by said second circular member.

4. The device of claim 1 wherein said means for directing comprises a second lens which focuses said scattered light onto said detector.

5. A device for detecting allergen particles in environmental air comprising:
   a light source having an optical axis wherein said light source directs a focused beam of light through a sample of said environmental air, whereby portions of said beam of light are scattered at various angles by particles of various sizes present in said sample of environmental air and whereby a portion of said beam of light remains unscattered;
   a first circular member centered on said optical axis, said first circular member being of a diameter greater than or equal to the diameter of said focused beam of light, said first circular member being opaque to light of the wavelength emitted by said light source;
   a second circular member centered on said optical axis, said second circular member being opaque to light of the wavelength emitted by said light source;
   a first lens which focuses noise generated by said light source onto said second circular member and which transmits said scattered light such that said scattered light is not blocked by said second circular member;
   a detector for measuring the quantity of light scattered by said particles in said sample of environmental air; and
   a second lens which focuses said scattered light onto said detector.

6. The device of claim 5 wherein said first circular member adheres to the center of said first lens and wherein said second circular member adheres to the center of said second lens.

7. The device of claim 6 wherein said first and second circular members are composed of darkened vinyl.

8. The device of claim 5 further comprising a generally tube-shaped housing having an inner surface finished to reflect a minimum of light wherein said light source, said first circular member, said second circular member, said first lens, said second lens and said detector are mounted within said housing.

9. The device of claim 8 further comprising a fan, mounted in an opening defined in said housing, said fan periodically refreshing said sample of environmental air.

10. The device of claim 9 wherein said fan periodically refreshes said sample of environmental air approximately every thirty seconds.

11. The device of claim 8 further comprising a circuit for generating an output alarm signal when one of a plurality of concentration levels of said particles has been detected.

12. The device of claim 11 wherein said concentration level is selectable by a user of said device.

13. The device of claim 11 wherein said detector produces an output voltage which is a function of the quantity of scattered light which is focused thereon and wherein said output voltage is converted to series of pulses and further comprising a counter which counts said pulses and generates said output alarm signal when a predetermined number of pulses are counted during a predetermined time period, said predetermined number of pulses being selectable by a user of said device.

14. The device of claim 11 wherein said output alarm signal is audible.

15. The device of claim 11 wherein said output alarm signal is visible.

16. The device of claim 11 wherein said output alarm signal turns on an air filter comprising one or more filtration elements and a blower to move air through said filtration elements.

17. The device of claim 16 wherein said air filter runs for a predetermined time period after being turned on by said alarm.

18. The device of claim 17 wherein said predetermined time period is selectable by a user of said device.

19. The device of claim 18 wherein said fan and said light source are inoperable during the time period when said air filter is operating.

20. The device of claim 16 wherein said air filter runs until said concentration of said particles in said sample of environmental air has returned below said one of said plurality of said concentration levels.

21. The device of claim 16 further comprising an ionizer which imparts a negative electrical charge to any particles remaining in air filtered by said air filter.

22. A method for detecting allergen particles in environmental air comprising:

obtaining a sample of said environmental air;

providing a light source to direct a light beam through said sample of air whereby portions of said beam of light are scattered at various angles by particles of various sizes present in said sample of air and whereby a portion of said beam of light remains unscattered;

blocking said unscattered portion of said beam of light;

blocking noise generated by said light source; and focusing said scattered portions of said beam of light onto a detector.

23. The method of claim 22 wherein said blocking of said noise is accomplished by focusing said noise and blocking said focused noise before said noise reaches said detector.

* * * * *